United States Patent [19]

Powers et al.

[11] Patent Number: 5,089,634
[45] Date of Patent: Feb. 18, 1992

[54] ISOCOUMARINS WITH CATIONIC SUBSTITUENTS

[75] Inventors: James C. Powers, Atlanta; Chih-Min Kam, Roswell, both of Ga.

[73] Assignee: Georgia Tech Research Corporation, Atlanta, Ga.

[21] Appl. No.: 530,158

[22] Filed: May 29, 1990

Related U.S. Application Data

[63] Continuation-in-part of Ser. No. 374,980, Jul. 3, 1989, Pat. No. 4,954,519, which is a continuation-in-part of Ser. No. 43,647, Apr. 28, 1987, Pat. No. 4,845,242, which is a continuation-in-part of Ser. No. 874,459, Jun. 13, 1986, abandoned, which is a continuation of Ser. No. 642,995, Aug. 20, 1984, Pat. No. 4,596,822.

[51] Int. Cl.$^5$ .......................................... C07D 31/365
[52] U.S. Cl. ...................................... 549/285; 549/283; 549/288; 549/289; 548/525; 548/336; 548/463; 548/822
[58] Field of Search ................ 549/283, 285, 288, 289

[56] References Cited

PUBLICATIONS

Kiyoaki et al., CA 88: 169969a.
Taknya et al., CA 104: 88435 V.

Primary Examiner—Jane T. Fan
Attorney, Agent, or Firm—Hurt, Richardson, Garner, Todd & Cadenhead

[57] ABSTRACT

Isocoumarins with cationic substituents, their use in inhibiting serine proteases with trypsin-like, chymotrypsin-like and elastase-like specificity and their roles as anticoagulant agents, and anti-inflammatory agents.

4 Claims, No Drawings

ISOCOUMARINS WITH CATIONIC SUBSTITUENTS

CROSS-REFERENCE TO RELATED APPLICATION

This application is a continuation-in-part of co-pending application Ser. No. 374,980, filed on July 3, 1989, which issued as U.S. Pat. No. 4,954,519 Sept. 4, 1990, which in turn was a continuation-in-part of application Ser. No. 43,647, filed on Apr. 28, 1987, which issued as U.S. Pat. No. 4,845,242 on July 4, 1989, which in turn was a continuation-in-part of application Ser. No. 874,459, filed on June 13, 1986, now abandoned, which in turn was a of application Ser. No. 642,995, filed on Aug. 20, 1984, which issued as U.S. Pat. No. 4,596,822 on June 24, 1986.

BACKGROUND OF THE INVENTION

1. Field of the Invention

This invention relates to a novel class of heterocyclic compounds useful for selectively inhibiting trypsin-like enzymes, selectively inhibiting chymotrypsin-like enzymes, selectively inhibiting elastase or for generally inhibiting serine proteases of all classes. This invention also relates to a method of controlling blood coagulation, complement activation, fibrinolysis, and tumor invasiveness and treating inflammation, blistering, and viral infection in patients using the novel compounds of the present invention. We have found that isocoumarins substituted with basic groups are potent inhibitors of blood coagulation enzymes, tryptases and plasmin, and isocoumarins substituted with hydrophobic groups are potent inhibitors of chymases and elastases, therefore they are useful as anticoagulants, anti-inflammatory and anti-tumor agents.

2. Description of the Related Art

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Blood coagulation serine proteases are responsible for vascular clotting, cerebral infarction, and coronary infarction. Plasmin and plasminogen activator are involved in tumor invasiveness, tissue remodeling, blistering, and clot dissociation. Uncontrolled proteolysis by elastases may cause pancreatitis, emphysema, rheumatoid arthritis, bronchial inflammation and adult respiratory distress syndrome. It has been suggested that a new trypsin-like cellular enzyme is involved in the infection of human immunodeficiency virus type 1 [HIV-1; Hattori et al., *FEBS Letters* 248, pp. 48–52 (1989)], which is a causative agent of acquired immunodeficiency syndrome (AIDS). Accordingly, specific and selective inhibitors of these proteases should be potent anticoagulants, anti-inflammtory agents, anti-tumor agents and anti-viral agents useful in the treatment of protease-related diseases [Powers and Harper, *Proteinase Inhibitors*, pp. 55-152 (Barrett and Salvesen, eds., Elsevier, 1986), incorporated herein by reference]. In vitro proteolysis by trypsin, chymotrypsin or the elastase family is a serious problem in the production, purification, isolation, transport or storage of peptides and proteins.

Anticoagulants and antithrombotic drugs are used in a variety of thrombotic disorders. The 1986 Physician's Desk Reference list three anticoagulant drugs (heparin, protamine sulfate and warfarin), one antiplatelet drug (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions [Von Kaulla, *Burger's Medicinal Chemistry*, Part II, pp. 1081-1132 (Wolff ed., 1979), incorporated herein by reference]. Coagulation disorders such as disseminated intravascular coagulation, bleeding complications of medical and surgical procedures and bleeding complications of systemic illness are still difficult to manage [Ingram, Brozovic and Slater, *Bleeding Disorders*, pp. 1–413 (Blackwell Scientific Publications, 1982), incorporated herein by reference]. In the treatment of patients with coagulation problems, anticoagulant or antithrombotic agents of diverse mechanisms are urgently sought in order to provide better medical care.

Anti-inflammatory agents are used to treat elastase-associated inflammation including rheumatoid arthritis and emphysema. Although the naturally occurring protease inhibitor, $\alpha 1$-protease inhibitor ($\alpha 1$-PI) has been used to treat patients with emphysema, this inhibitor is not widely used clinically due to the high dosage needed for the treatment and difficulty of producing large quantities. Therefore small molecular weight elastase inhibitors are needed for therapy.

SUMMARY OF THE INVENTION

It is an object of this invention to define a novel group of specific inhibitors for trypsin, elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to define new protease inhibitors, especially blood coagulation enzyme inhibitors, which can act as anticoagulants in vitro and in vivo. Such inhibitors could be used in prevention of thrombosis during periods of stasis and/or endothelial damage is segments of vasculature. They could also be used in an adjunct to fibrinolytic therapy to prevent acute coronary or peripheral artery reclosure. The inhibitors of this invention would be useful as the sole method of maintaining anticoagulation in extracorporeal blood circuits such as the kidney hemodialysis, and heart lung bypass. Such inhibitors could also be used as alternate anticoagulants when conventional anticoagulation with heparin or coumarin fail or is contraindicated. The inhibitors of this invention would also be useful in the therapy for disseminated intravascular coagulation syndromes (DIC). They could also be used in prophylaxis against thrombosis in high risk situation involving myocardium (e.g. unstable angina).

It is another object of this invention to define new protease inhibitors, especially elastase inhibitors, tryptase inhibitors, chymase inhibitors and plasmin inhibitors. These inhibitors are useful for controlling tissue damage and various inflammatory conditions mediated by proteases particularly elastases. The inhibitors of this invention would be useful for treating diseases related to plasmin; such as tumor invasiveness and blistering. The inhibitors of this invention would also be useful for controlling hormone processing by serine proteases and for treating related to tryptases and chymases such as inflammation and skin blistering. The inhibitors of this invention are useful for treating diseases related to tryptases and caused by viral infection such as AIDS.

It is a further object of this invention to define a novel group of specific inhibitors useful in vitro for inhibiting trypsin, elastase, chymotrypsin and other serine proteases of similar specificity and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Isocoumarins with cationic substituents have been found to be excellent inhibitors of several serine proteases including bovine thrombin, human thrombin, human factor Xa, human factor XIa, human factor XIIa, bovine trypsin, human plasma plasmin, human tissue plasminogen activator, human lung tryptase, rat skin tryptase, human leukocyte elastase, porcine pancreatic elastase, bovine chymotrypsin and human leukocyte cathepsin G. These compounds inhibit the serine proteases by reaction with active site serine to form an acyl enzyme, which in some cases may further react with another active site nucleophile to form an additional covalent bond. These structures may be used in vivo to treat diseases resulting from uncontrolled blood coagulation or disease caused by uncontrolled proteolysis by elastase, chymotrypsin, trypsin and related serine proteases. These inhibitors may be used in vitro to prevent proteolysis which occurs in the process of production, isolation, purification, storage and transport of peptides and proteins. The novel substituted isocoumarin and related heterocyclic compounds have the following structural formula:

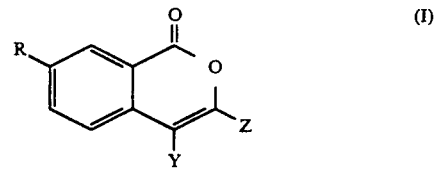

or a pharmaceutically acceptable salt, wherein
Z is selected from the group consistsing of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with an guanidino group attached to the alkyl group, $C_{1-6}$ alkyl with an amidino group attached to the alkyl group, R is selected from the group consisting of O=C=N—, S=C=N—, AA—NH—, AA—AA—NH—, AA—O—, AA—AA—O—, M—NH—, M—AA—NH—, M—AA—AA—NH—, M—O—, M—AA—O—, M—AA—AA—O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, alpha-aminobutyric acid, epsilonaminocaproic acid, citrulline, hydroxyproline, ornithine or sarcosine, wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—, wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, or $C_{1-6}$ alkyl-O-CO-, wherein K represents halogen, COOH, OH, CN, $NO_2$, $NH_2$, $C_{1-6}$ alkoxy, $C_{1-6}$ alkylamine, $C_{1-6}$ dialkylamine, or $C_{1-6}$ alkyl-O-CO-, Y is selected from the group consisting of H, halogen, trifluoromethyl, methyl, OH and methoxy, The compounds of Formula (I) can also contain one or more substituents at position B as shown in the following structure:

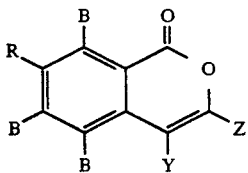

wherein electronegative substituents for position B such as $NO_2$, CN, Cl, COOR, and COOH will increase the reactivity of the isocoumarin, and electropositive substituents such as $NH_2$, OH, alkoxy, thioalkyl, alkyl, alkylamino, and dialkylamino will increase its stability. Neutral substituents could also increase the stability of acyl enzyme and improve the effectiveness of the inhibitors.

Other substituted isocoumarins have been prepared earlier for other purposes (illustrative examples: 3-chloroisocoumarin, Davies and Poole, *J. Chem. Soc.*, pp. 1616–1629 (1928); 3-chloro and 3,4-dichloroisocoumarin, Milevskaya, Belinskaya, and Yagupol'skii, *Zhur. Org. Khim.* 9, pp. 2145–2149 (1973); 3-methyl and 4-carboxy-3-methylisocoumarin, Tirodkar and Usgaonkar, *Ind. J. Chem.* 7, pp. 1114–1116 (1969); 7-nitro and 7-aminoisocoumarin, Choksey and Usgaonkar, *Ind. J. Chem.* 14B, pp. 596–598 (1976), the preceding articles are incorporated herein by reference).

A number of other substituted isocoumarins have been prepared recently for inhibition of serine proteases (3-chloroisocoumarin, Harper, Hemmi, and Powers, *J. Am. Chem. Soc.* 105, pp. 6518–6520 (1983); 3,4-dichloroisocoumarin, Harper, Hemmi, and Powers, *Biochemistry* 24, pp. 1831–1841 (1985); 3-alkoxy-7-amino-4-chloroisocoumarin, Harper and Powers, *J. Am. Chem. Soc.* 106, pp. 7618–7619 (1984), Harper and Powers, *Biochemistry* 24, 7200–7213 (1983); substituted isocoumarins with basic groups (aminoalkoxy, guanidino or isothiureidoalkoxy), Kam, Fujikawa and Powers, *Biochemistry* 27, pp. 2547–2557 (1988); 7-substituted 3-alkoxy-4-chloroisocoumarins, Powers, Kam, Narasimhan, Oleksyszyn, Hernandez and Ueda, *J. Cell Biochem.* 39, pp. 33–46 (1989), Powers, Oleksyszyn, Narasimhan, Kam, Radhakrishnan and Meyer, Jr. *Biochemistry* 29, pp. 3108–3118 (1990), the preceding articles are incorporated herein by reference; Powers and Harper, U.S. Pat. No. 4,596,822; Powers and Kam, U.S. Pat. No. 4,845,242 which are also incorporated by reference).

The following compounds are representative of but do not limit the invention:

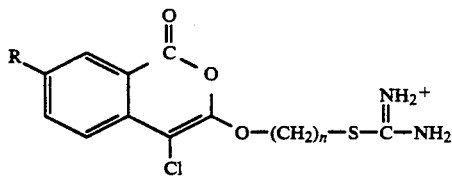

CiTEtOIC (n=2); CiTPrOIC (n=3)

7-(benzylcarbamoylamino)-4-chloro-3-(3-isothiureidopropoxy)isocoumarin (PhCH₂NHCONH-CiTPrOIC)
7-(phenylcarbamoylamino)-4-chloro-3-(3-isothiureidopropoxy)isocoumarin (PhNHCONH-CiTPrOIC)
7-(acetylamino)-4-chloro-3-(3-isothiureidopropoxy)isocoumarin (CH₃CONH-CiTPrOIC)
7-(3-phenylpropionylamino)-4-3-(3-isothiureidopropoxy)isocoumarin (PhCH₂CH₂CPNH-CiTPrOIC)
7-(phenylacetylamino)-4-chloro-3-(3-isothiureidopropoxy)isocoumarin (PhCH₂COHNH-CiTPrOIC)
7-(L-phenylalanylamino)-4-chloro-3-(3-isothiureidopropoxy)isocoumarin (L-Phe-NH-CiTPrOIC)
7-(N-t-butyloxycarbonyl-L-phenylalanylamino)-4-chloro-3-(3-isothiureidopropoxy)isocoumarin (Boc-L-Phe-NH-CiTPrOIC)
7-(D-phenylalanylamino)-4-chloro-3-(3-isothiureidopropoxy)isocoumarin (D-Phe-NH-CiTPrOIC)
7-(N-t-butyloxycarbonyl-D-phenylalanylamino)-4-chloro-3-(3-isothiureidopropoxy)isocoumarin (Boc-D-Phe-NH-CoTPrOIC)
7-(benzylcarbamoylamino)-4-chloro-3-(2-isothiureidoethoxy)isocoumarin )PhCH₂NHCONH-CiTEtOIC)
7(phenylcarbamoylamino)-4-chloro-3-(2-isothiureidoethoxy)isocoumarin (PhNHCONH-CiTEtOIC)
7(isopropylcarbamoylamino4-chloro-3-(2-isothiureidoethyxy)isocoumarin ((CH₃)₂CHNHCONH-CiTEtOIC)
7-phenylacetylamino)-4-chloro-3-(2isothiureidoethoxy)isocoumarin )PhCH₂CONH-CiTEtOIC)
7-(L-phenylalanylamino)-4-chloro-3-(2-isothiureidoethoxy)isocoumarin (L-Phe-NH-CiTEtOIC)
7-(N-t-butyloxycarbonyl-L-phenylalanylamino)-4-chloro-3-(2-isothiureidoethoxy)isocoumarin (Boc-L-Phe-NH-CiTEtOIC)
7-(D-phenylalanylamino)-4-chloro-3-(2-isothiureidoethoxy)isocoumarin (D-Phe-NH-CiTEtOIC)
7-(N-t-butyloxycarbonyl-D-phenylalanylamino)-4-chloro-3-(2-isothiureidoethoxy)isocoumarin (Boc-D-Phe-NH-CiTEtOIC)
7-(N-t-butyloxycarbonyl-L-alanyl-L-alanylamino)-4-chloro-3-(2-isothiureidoethoxy)isocoumarin (Boc-Ala-Ala-NH-CiTEtOIC)
7-(L-alanyl-L-alanylamino)-4-chloro-3-(2-isothiureidoethoxy)isocoumarin (Ala-Ala-NH-CiTEtOIC)
7-(1-naphthylcarbamoylamino)-4-chloro-3-(2-isothiureidoethoxy)isocoumarin (NaphthylNH-CiTEtOIC)
7-((S)-α-methylbenzylcarbamoylamino)-4-chloro-3-(2-isothiureidoethoxy)isocoumarin (S-C₆H₅(CH₃)CHNHCONH-CiTEtOIC)
7-((R)-α-methylbenzylcarbamoylamino)-4-chloro-3-(2-isothiureidoethoxy)isocoumarin (R-C₆H₅(CH₃)CHNHCONH-CiTEtOIC)
7-dansylamino-4-chloro-3-(2-isothiureidoethoxy)isocoumarin (DansylNH-CiTEtOIC)
7-phenylthiocarbamoylamino-4-chloro-3-(2-isothiureidoethoxy)isocoumarin (PhNHCSNH-CiTEtOIC)
7-(m-carboxyphenylthiocarbamoyl)amino-4-chloro-3-(2-isothiureidoethoxy)isocoumarin (m-COOH-PhNHCSNH-CiTEtOIC)
7-(p-carboxyphenhylthiocarbamoyl)amino-4-chloro-3-(2-isothiureidoethoxy)isocoumarin (p-COOH-PhNHCSNH-CiTEtOIC)

It has been found that compounds of Formula (I) have anticoagulant activity as shown in Table I by effective inhibition of the proteolytic function of blood coagulation enzymes in Hepes buffer. Compounds of Formula (I) also have anticoagulant effect in vitro as shown in Table IV by prolongation of the prothrombin time (PT) and activated partial thromboplastin time (APTT) in pig plasma. Compounds of Formula (I) are effective in the detection, prevention and inhibition of adult and infantile respiratory distress syndrome (a consequence of acute lung injuries) as shown in Table II by the effective inhibition of the proteolytic function of human lung tryptase. Sheep lung lymph tryptase is utilized as a marker of lung capillary injury, and this is shown in the articles by Lesser et al., *Am. Rev. Respir. Dis.* 135, pp. 643-650 (1987) and by Orlowski et al., *Arch.Biochem. Biophys.* 269, pp. 125-136 (1989), which are incorporated herein by reference. Compounds of Formula (I) are effective in treating a variety of blistering diseases as shown in Table II by the effective inhibition of proteolytic function of rat skin tryptase and human skin tryptase. It has been found that compounds of Formula (I) have anti-tumor activity as shown in Table II by the effective inhibition of the proteolytic function of human plasma plasmin and human tissue plasminogen activator. Compounds of Formula (I) have anti-inflammatory activity and are effective in the treatment of pulmonary emphysema and adult respiratory distress syndrome as shown in Table III by the effective inhibition of the proteolytic function of human leukocyte elastase.

In activation rates of serine proteases by substituted isocoumarins were measured by the incubation method. An aliquot of inhibitor (25 or 50 $\mu$l) in Me$_2$SO was added to a buffered enzyme solution (0.01-2.3 $\mu$M) to initiate the inactivation. Aliquots (50 $\mu$l) were withdrawn at various intervals and the residual enzymatic activity was measured. Me$_2$SO concentration in the reaction mixture was 8-12% (v/v). 0.1 Hepes, 0.01M CaCl$_2$, pH 7.5 buffer was utilized for trypsin and coagulation enzymes. 0.1M Hepes, 0.5M NaCl, pH 7.5 was utilized for other serine proteases. The inhibitor concentrations are shown in the Tables I, II, III, and IV. Peptide thioesters or peptide nitroanilides with appropriate sequence were used as substrates for various serine proteases. All peptide thioester hydrolysis rates were measured with assay mixtures containing 4,4'-dithiodipyridine ($\epsilon_{324}$=19800 M$^{-1}$cm$^{-1}$; Grasetti & Murray, *Arch. Biochem. Biophys.* 119, pp. 41-49 (1967), incorporated herein by reference). Peptide 4-nitroanilide hydrolysis was measured at 410 nm ($\epsilon_{410}$=8800 M$^{-1}$cm$^{-1}$; Erlanger et al., *Arch. Biochem. Biophys.* 95, pp. 271-278 (1961), incorporated herein by reference). First order inactivation rate constants (k$_{obs}$) were obtained from plots in ln (v$_t$/v$_o$) vs time, and the correlation coefficients were greater than 0.98.

When the isocoumarin structure contains a basic functional group such as isothiureidoalkoxy as Z, substituted amino as R and Cl as Y, the compound is generally a good inhibitor for trypsin, blood coagulation enzymes and other tryptases. The inactivation of the enzyme is time dependent, and the k$_{obs}$/[I] values are second order rate contstants. In most cases, inactivation of the enzyme occurs at the inhibitor concentration of 5-400 times the enzyme concentration and the first order rate constant k$_{obs}$ is obtained. The inactivation rate of the enzyme depends on the substituents R, Y and Z. Table I shows the inactivation rate constants for trypsin and blood coagulation enzymes inhibited by substituted isocoumarins. The isocoumarins with R groups of phenylcarbamoylamino or S-methylbenzylcarbamoylamino, Y group of Cl and Z group of isothiureidoethoxy are the best inhibitors toward bovine and human thrombin. The isocoumarin with R group of phenylcarbamoylamino, Y group of Cl and Z group of isothiureidoethoxy is the potent inhibitor for human factor Xa and human factor XIa. The isocoumarin with R group of L-Phe, Y group of Cl and Z group of isothiureidoethoxy is the best inhibitor for human factor XIIa.

Table II shows the inactivation of human lung tryptase, human skin tryptase and rat skin tryptase by substituted isocoumarins. The structures with R groups of substituted amino, Y group of Cl, and Z group of isothiureidoalkoxy are good inhibitors for all three tryptases. Table II also shows the inactivation rate constants for human plasmin and human tissue plasminogen activator by these substituted isocoumarins. The structure with R groups of substituted amino, Y groups of Cl, and Z group of isothiureidoalkoxy inhibited both enzymes potently. Table III shows the inactivation rate constants of porcine pancreatic elastase (PPE), human leukocyte elastase (HLE), chymotrypsin and cathepsin G inhibited by substituted isocoumarins. Although the inactivation by these inhibitors was less efficient toward PPE and cathepsin G than trypsin-like enzymes, the structure with R group of phenylcarbamoylamino, Y group of Cl, and Z group of isothiureidoethoxy is a potent inhibitor of HLE. The structure with R group of phenylacetylamino, Y group of Cl, and Z-group of isothiureidopropoxy is best at inhibiting chymotrypsin.

The spontaneous hydrolysis rate of these substituted isocoumarins in Hepes buffer have been measured and are summarized in Table V. The isocoumarins substituted with phenylcarbamoylamino or benzylcarbamoylamino at the 7-position are more stable than 7-amino-4-chloro-3-(3-isothiureidopropoxy)isocoumarin. The isocoumarins substituted with 7-alkanoylamino group are less stable than the parent 7-amino compound.

Table IV shows the anticoagulant effect of substituted isocoumarins in pig plasma. The prothrombin time (PT) and activated partial thromboplastin time (APTT) were measured in the presence of various inhibitors. 7-(Phenylcarbamoylamino)-4-chloro-3-(2-isothiureidoethoxy)isocoumarin prolong PT 3.1 fold at 32 $\mu$M, and it also prolongs APTT more than 6.8 fold at 16 $\mu$M. 7-(Benmzylcarbamoylamino)-, or 7-($\alpha$-methylbenzylcarbamoylamino)-3-(2-isothiureidoethoxy)-4-chloroisocoumarin prolongs APTT more than 6.8 fold and increases PT 1.5 fold at 32 $\mu$M.

Anticoagulants can prolong the clotting time of human plasma and play important roles in the treatment of blood coagulation related diseases such as vascular clotting, cerebral infarction and coronary infarction [Williams et al. *Hematology*, 3rd ed. (McGraw Hill, 1983) and Ingram et al. *Bleeding Disorders*, 2nd ed. (Blackwell Scientific Publications, 1985). These two books are incorporated herein by reference]. The presence of certain inhibitors of this invention in pig plasma prolong the prothrombin time and activated partial thromboplastin time quite effectively, therefore these compounds act as anticoagulants in vitro. Currently, there are few anticoagulant and antithrombotic drugs in use clinically, and the inhibitors described in this invention can be used as anticoagulants or antithrombotics in mammals (including man).

Considerable evidence has been shown that plasminogen activator, leukocyte elastase and/or related enzymes play a role in tumor cell metastasis [Salo, et al., *Int. J. Cancer* 30, pp. 669-673 (1973); Kao et al., *Biochem. Biophys. Res. Comm.* 105, pp. 383-389 (1982); Powers, J. C. *Modification of Proteins*, R. e. Feeney and J. R. Whitaker, eds., Adv. Chem. Ser. 198, pp. 347-367

(Amer. Chem. Soc., Wash., D.C. 1982)], therefore it is suggested that compounds of this invention may have anti-tumor activity.

Pulmonary emphysema is a disease characterized by progressive loss of lung elasticity die to the destruction of lung elastin and alveoli. The destructive changes of lung parentchyma associated with pulmonary emphysema are caused by uncontrolled proteolysis in lung tissues (Janoff, *Chest* 83 pp. 54–58 (1983), incorporated herein by reference). A number of proteases have been shown to induce emphysema in animals [Marco et al., *Am. Rev. Respir. Dis.* 104, pp. 595–598 (1971); Kaplan, *J. Lab. Clin. Med.* 82, pp. 349–356 (1973), these two articles are incorporated herein by reference], particularly human leukocyte elastase [Janoff, ibid 115, pp. 461–478 (1977), incorporated herein by reference]. Leukocyte elastase and other mediators of inflammation also appear to play a role in diseases such as mucocutaneous lymph node syndrome [Reiger et al., *Eur. J. Pediatr.* 140, pp. 92–97 (1983), incorporated herein by reference] and adult respiratory distress syndrome [Stockley, *Clinical Science b* 64, pp. 119–126 (1983); Lee et al., *N. Eng. J. Med.* 304, pp. 192–196 (1981); Rinaldo, ibid 301, 900–909 (1982), all these articles are incorporated herein by reference].

It is known that in vitro activity of elastase inhibitors correlates with in vivo activity in animal models of emphysema and inflammation (Otterness et al., editors, *Advances in Inflammation Research*, Vol. 11, (Raven Press 1986), and this article is incorporated herein by reference). Prophylactic administration of an inhibitor of elastase significantly diminishes the extent of elastase-induced emphysema [Kleinerman et al., *Am. Rev. Respir. Dis.* 121, pp. 381–387 (1980); Lucey et al., *Eur. Respir. J.* 2, pp. 421–427 (1989)]. Thus the novel inhibitors described here should be useful for the treatment of emphysema and inflammation. Elastase inhibitors have been used orally, by injection or by instillation in the lungs in animal studies (Powers, *Am. Rev. Respir. Dis.*, 127, s54–s58 (1983); Powers and Bengali, *Am. Rev. Respir. Dis.* 134, pp. 1097–1100 (1986) and these two articles are incorporated herein by reference). The inhibitors described above can be used by any of these routes.

For treatment of blood coagulation-related diseases, tumor invasiveness, viral infection or inflammation, the compounds of Formula (I) or pharmaceutically acceptable salts may be administered orally, topically or parenterally. The term parenteral as used includes subcutaneous injection, intravenous, intramuscular, injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches. lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the compounds of Formula (I) or their pharmaceutically acceptable salts will normally be in the dosage range from 0.2 to 140 mg/kg of body weight. Administration is made by intravenous, intramuscular or subcutaneous injection. Accordingly, pharmaceutical compositions for parenteral administration will contain in a single dosage form about 10 mg to 7 gms of compounds of Formula (I) per dose. In addition to the active ingredient, these pharmaceutical composition will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspension. A composition in the form of an aqueous solution is obtained by dissolving the compounds of Formula (I) or their pharmaceutically acceptable salts in aqueous buffer solution of pH 4 to 6.5 and if desired, adding a polymeric binder. An oily formulation for topical application is obtained by suspending the compound of Formula (I) or their pharmaceutically acceptable salts in a oil, optionally with the addition of a swelling agent such as aluminium stearate and/or a surfactant.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspensions. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma and would make purification of the proteins easier. The inhibitors disclosed here could be used in cloning experiments utilizing bacterial cultures, yeast and purified cloned product in higher yield.

The following examples are given to illustrate the invention and are not intended to limit it in any manner.

EXAMPLE 1

Preparation of 7-(phenylcarbamoylamino)-4-chloro-3-(2-isothiureidoethoxy)isocoumarin 7-Amino-3-(2-bromoethoxy)-4-chloroisocoumarin was synthesized as previously described (Powers et al., *Biochemistry* 29, pp. 3108–3118 (1990), incorporated herein by reference). This compound (0.32 g, 1 mmole) was mixed with phenyl isocyanate (0.12 g, 1 mmole) in 5 91 ml of THF and the reaction mixture was stirred at room temperature overnight. The product 7-(phenylcarbamoylamino)-4-chloro-3-(2-bromoethoxy)isocoumarin precipitated out, yield 40%, melting point (m.p.) 215°–217° C., mass spectrum m/e =437.9(M+). Anal. Calc. for $C_{18}H_{14}N_2O_4ClBr$:C,49.40; H, 3.22; N, 6.40; Cl, 8.10. Found: C,49.48; H, 3.25; N,6.34; Cl, 8.12. The phenylcarbamoylamino compound (0.1 g, 0.23 mmole) was heated with 0.02 g of thiourea (0.26 mmole) in 10 ml of THF at 70° C. overnight. The final product precipitated out, yield 0.04 g, 36%, m.p. 161°–163° C. (dec.), mass spectrum (FAB+)m/e=433(M-Br). Anal. Calc. for $C_{19}H_{18}N_4O_4ClBrS\cdot 0.25$ THF: C, 45.12; H, 3.86; N, 10.53; Cl, 6.67. Found: C, 44.83; H, 3.92; N, 10.12; Cl, 6.41.

7-(Ethylcarbamoylamino)-4-chloro-3-(2-isothiureidoethoxy)isocoumarin, 7-(t-butylcarbamoylamino)-4-chloro-3-(2-isothiureidoethoxy)isocoumarin, 114 7-(benzylthiocarbamoylamino)-4-chloro-3-(2-isothiureidoethoxy)isocoumarin, 7-(ethylthiocarbamoylamino)-4-chloro-3-(2isothiureidoethoxy)isocoumarin, 7-(4-fluorobenzyl)thiocarbamoylamino-4-chloro-3-(2-isothiureidoethoxy)isocoumarin, and 7-(2,5-dimethylbenzyl)thiocarbamoylamino-4-chloro-3-(2-isothiureidoethoxy)isocoumarin can be prepared by using the appropriate isocyanate or isothiocyanate.

EXAMPLE 2

Preparation of 7-(acetylamino)-4-chloro-3-(3-isothiureidopropoxy)isocoumarin

7Amino-3-(3-bromopropoxy)-4-chloroisocoumarin was synthesized as previously described (Kam et al., 1988). This compound (0.33 g, 1 mmole) was heated with 0.15 g of acetic anhydride (1.5 mmole) in 20 ml of dry THF. After a few minutes, a yellow solid precipitated out. After 3 hrs, the solution was concentrated to 5 ml, and the solid was filtered to give 0.37 g of 7-(acetylamino)-4-chloro-3-(3-bromopropoxy)isocoumarin, m.p. 170°-172° C.; mass spectrum: m/e=375(m+). The acetylated isocoumarin (0.15 g, 0.4 mmole) was treated with thiourea (0.036 g, 0.47 mmole) to give 0.9 g of the final product, (yield 50%), m.p. 180°-181° C., mass spectrum m/e=370 (M+-Br). Anal. Calc. for $C_{15}H_{17}N_3O_4ClBrS$: C, 39.97; H, 3.80; N, 9.32; Cl 7.87. Found: C, 39.86; H 3.83; N, 9.29; Cl, 7.85.

7-Trifluoroacetylamino-4-chloro-3-(3-isothiureidopropoxy)isocoumarin, 7-heptafluorobutyroylamino-4-chloro-3-(3-isothiureidopropoxy)isocoumarin, 7-succinylamino-4-chloro-3-(3-isothiureidopropoxy)isocoumarin, and 7-(o-phthalyl)amino-4-chloro-3-(3-isothiureidopropoxy)isocoumarin can be prepared by using the appropriate anhydride.

EXAMPLE 3

Preparation of 7-(benzylcarbamoylamino)-4-chloro-3-(3-isothiureidopropoxy)isocoumarin 7-(benzylcarbamoylamino)-4-chloro-3-(3-bromopropoxy)isocoumarin was prepared from the reaction of benzyl isocyanante with 7-amino-4-chloro-3-(3-bromopropoxy)isocoumarin as described above, m.p. 188°-189° C., mass spectrum: m/e=359(M+-benzyl). The final product was obtained from the reaction of 7-(benzylcarbamoylamino)-4-chloro-3-(3-bromopropoxy)isocoumarin with thiourea as described above (yield 74%). m.p. 165°-166° C.; mass spectrum (FAB+) m/e=461(M+-Br). Anal Calc. for $C_{21}H_{22}N_4O_4ClBrS \cdot 0.75$ THF: C, 48.36; H, 4.70; N, 9.40; Cl, 6.56. Found; C, 48.13; H, 4.87; N, 9.65; Cl,6.15.

EXAMPLE 4

Preparation of 7-(phenylacetylamino)-4-chloro-3--(2-isothiureidoethoxy)isocoumarin 7-Amino-4-chloro-3-(2-bromoethoxy)isocoumarin (0.15 g, 0.47 mmole) was first mixed with phenylacetyl chloride (0.09 g, 0.55 mmole) in 10 ml of THF, triethylamine (0.05 g, 0.47 mmole) was then added and the reaction mixture was stirred at room temperature overnight. After $Et_3N \cdot HCl$ salt was removed by filtration, the product 7-(phenylacetylamino)-4-chloro-3-(2-bromoethoxy)isocoumarin 142 was crystallized from THF and Petroleum ether (yield, 73%), m.p. 165°-169° C.; mass spectrum; m/e=436.7(M+). The phenylacetyamino derivative (0.1 g) was heated with thiourea (0.02 g) to give the product 0.05 g (yield, 40%), m.p. 115°-120° C.; mass spectrum FAB+) m/e=432(M+-Br). Anal. Calc. for $C_{20}H_{19}N_3O_4ClBrS \cdot 0.5$ $H_2O$: C 45.99; H, 3.83; N, 8.05; Cl, 6.80. Found: C, 46.09; H, 4.17; N, 8.02; Cl, 6.79.

EXAMPLE 5

Preparation of 7-(R-α-methylbenzylcarbamoylamino)-4-chloro-3-(2-isothiureidoethoxy)isocoumarin 7-R-α-methylbenzylcarbamoylamino)-4-chloro-3-(2-bromoethoxy)isocoumarin was synthesized in the same manner as described above, m.p. 183°-185° C.; mass spectrum m/e=464 (M+). This compound (0.1 g) reacted with thiourea (0.02 g) under the same condition described above to form the final product 7-(R-α-methylbenzylcarbamoylamino)-4-chloro-3-(2-isothiureidoethoxy)isocoumarin (0.078 g), m.p. 143°-150° C.; mass spectrum FAB)+) m/e=461 ($M^{30}$-Br). Anal. Calc. for $C_{21}H_{22}N_4O_4ClBrS \cdot 0.5H_2O$: C, 45.75; H, 4.35; N, 10.17; Cl, 6.44. Found: C, 44.95; H, 4.31; N, 10.02; Cl 6.36.

EXAMPLE 6

Preparation of 7-(D-phenylalanylamino)-4-chloro-3-(2-isothiureidoethoxy)isocoumarin Boc-D-Phe (0.33 g, 1.2 mmole) reacted with 1,3-dicyclohexylcarbodiimide (0.13 g, 0.6 mmole) in 10 ml THF at 0° C. for 1 hr to form the symmetric anhydride, and then 7-amino-4-chloro-3-(2-bromoethoxy)isocoumarin (0.2 171 g, 0.6 mmole) was added. The reaction was stirred at room temperature overnight and the precipitate 7-(Boc-D-Phe-amino)-4-chloro-3-(2-bromeothoxy)isocoumarin was formed (0.29 g, 71%). Thin layer chromatography (TLC) one spot, m.p. 180°-182° C.; mass spectrum m/e=566 (M+). Anal Calc. for $C_{25}H_{26}N_2O_6ClBr$: C, 53.07; H, 4.63; N, 4.95; Cl 6.27. Found: C, 53.25; H 4.66; N, 4.87; Cl, 6.24. Boc-D-Phe compound (0.2 g, 0.35 mmole)was reacted with thiourea (0.027 g, 0.35 mmole) in the same manner to give 7-(Boc-D-phenylalanylamino)-4-chloro-3-(2-isothiureidoethoxy)isocoumarin (0.14 g), yield 62%, mass spectrum (FAB+) m/e 561 (M+-Br). This compound was dissolved in 3 ml of THF at 0° C. and then the solvent was evaporated to dryness. The final product precipitated out after addition of ether, one spot on TLC ($CH_3CN:H_2O:AcOH=8:1:1$); mass spectrum (FAB+) m/e 462 (M+-Br—$CF_3COO$).

7-Boc-alanylamino-4-chloro-3-(2isothiureidoethoxy)isocoumarin, 7-benzoyl-alanyllamino-4-chloro-3-(2Isothiureidoethoxy)isocourmarin, 7-benzoylphenylalanylamino-4-chloro-3-(2-isothiureidoethoxy)isocoumarin and 7-Boc-valyamino-4-chloro-3-(2-isothiureidoethoxy)isocoumarin can be prepared by using appropriate Boc-amino acid or benzoyl-amino acid derivative.

EXAMPLE 7

Preparation of
7-(Boc-alanylalanylamino)-4-chloro-3-(2-isothiureidoethoxy)isocoumarin 7-Boc-alanylalanylamino)-4-chloro-3-(2-bromeothoxy)isocoumarin was synthesized in the same manner, m.p. 147°–151° C.; mass spectrum m/e=561 (M+). Anal. Calc.: C, 47.12; H, 4.85. Found: C, 4.87. This compound (0.2 g) was reacted with thiourea (0.03 g) by the same procedure to form 7-(Boc-alanylalanylamino)-4-chloro-3-(2-isothiureidoethoxy)isocoumarin (0.04 g), mass spectrum m/e=556 (M+-Br).

7-Alanylalanylamino-4-chloro-3-(2-isothiureidoethoxy)isocoumarin was prepared by deblocking of Boc-Ala-Ala-NH-CiTEtOIC with trifluoracetic acid, mass spectrum (FAB+) m/e456 (M+-Br—CF$_3$COO).

EXAMPLE 8

Preparation of
7-(phenylthiocarbamoylamino)-4-chloro-3-(2-isothiureidoethoxy)isocoumarin 7-(Phenylthiocarbamoylamino)-4-chloro-3-(2-bromoethoxy)isocoumarin was prepared from the reaction of phenyl isothiocyanate with 7-amino-4-chloro-3-(2-bromoethoxy)isocoumarin, yield 59%, m.p. 157°–158° C.; mass spectrum m/e 361 (m+-PhNH+1). Anal. Calc.: C, 48.36; H, 3.39. Found: C, 48.26; H, 3.40. The bromoethoxy compound was then reacted with thiourea by the same procedure to give the final product, yield 32%, mass spectrum (FAB+) m/e 449 (M+-Br).

EXAMPLE 9

Preparation of
7-(m-carboxyphenylthiocarbamoylamino)-4-chloro-3-(2-isothiureidoethoxy)isocoumarin 7-(m-Carboxyphenylthiocarbamoylamino)-4-chloro-3-(2-bromoethoxy)isocoumarin was prepared from the reaction of m-carboxyphenyl isothiocyanate with 7-amino-4-chloro-3-(2-bromeothoxy)isocoumarin, yield 64%, m.p. 157°–158° C.; mass spectrum m/e 361 (M+-(COOH)PhNH+1). Anal. Calc.: C, 45.85; H, 2.84. Found: C, 45.73; H, 2.86. The bromoethoxy compound was then reacted with thiourea to give the product, yield 21%; mass spectrum (FAB+) m/e/ 493 (M+-Br).

7-(3-Fluorobenzoyl)amino-4-chloro-3-(2-isothiureidoethoxy)isocoumarin, 7-(3-nitrobenzoyl)amino-4-chloro-3-(2isothiureidoethoxy)isocoumarin, 7-(3-phenylpropionyl)amino-4-chloro-3-(2-isothiureidoethoxy)isocoumarin, 7-diphenylacetylamino-4-chloro-3-(2-isothiureidoethoxy)isocoumarin, 7-diphenylpropionylamino-4-chloro-3-(2-isothiureidoethoxy)isocoumarin, 7-(p-toluenesulfonyl)amino-4-chloro-3-(2-isothiureidoethoxy)isocoumarin, and 7-(α-toluenesulfonyl)amino-4-chloro-3-(2-isothiureidoethoxy)isocoumarin can be prepared from the reaction of corresponding 7-substituted-4-chloro-3-(2-bromoethoxy)isocoumarin with thiourea as described above. 7-substituted-4-4chloro-3-(2-bromeothoxy)isocoumarin can be synthesized by reacting 7-amino-4-chloro-3-(2-bromeothoxy)isocoumarin with appropriate acid chloride or sulfonyl chloride in the presence of Et$_3$N.

7-Ethoxycarbonylamino-4-chloro-3-(2-isothiureidoethoxy)isocoumarin, 7-benzyloxycarbonylamino-4chloro-3-(2-isothiureidoethoxy)isocoumarin, and 7-phenoxycarbonylamino-4-chloro-3-(2-isothiureidoethoxy)isocoumarin can be prepared from the reaction of 7-substituted-4-chloro-260 3-(2-bromeothoxy)isocoumarin with thiourea. 7-Ethoxycarbonylamino-4-chloro-3-(2-bromeothoxy)isocoumarin, 7-benzyloxycarbonylamino-4-chloro-3-(2-bromeothoxy)isocoumarin and 7-phenoxycarbonylamino-4-chloro-3-(2-bromeothoxy)isocoumarin can be synthesized by reacting 7-amino-4-chloro-3-(2-bromeothoxy)isocoumarin with the corresponding chloroformate.

TABLE 1

Inhibition Rates of Bovine Trypsin and Coagulation Enzymes by 7-Substituted-4-chloro-3-isothiureidoalkoxyisocoumarins[a].

| | $k_{obs}/[I]$ $(M^{-1}s^{-1})$ | | | | | |
|---|---|---|---|---|---|---|
| Compounds | Bovine Trypsin[b] | Bovine Thrombin[c] | Human Thrombin[d] | Human Factor Xa[e] | Human Factor XIa[f] | Human Factor XIIa[g] |
| NH$_2$-CiTPrOIC | 410,000[h] | 630[h] | 760 | 60[h] | 22,000[h] | 6,200[h] |
| PhCH$_2$NHCONH-CiTPrOIC | 51,000 | 420 | 700 | | | |
| PhNHCONH-CiTPrOIC | 63,000 | 970 | 1,840 | 50 | | 7,720 |
| CH$_3$CONH-CiTPrOIC | 107,000 | 420 | 310 | | | |
| PhCH$_2$CH$_2$CONH-CiTPrOIC | 87,900 | 820 | 630 | | | |
| PhCH$_2$CONH-CiTPrOIC | 165,000 | 600 | 610 | | | |
| L-Phe-NH-CiTPrOIC | | 400 | 470 | | | |
| Boc-L-Phe-NH-CiTPrOIC | | 330 | 520 | | | |
| D-Phe-NH-CiTPrOIC | 68,300 | 180 | 220 | | | |
| Boc-D-Phe-NH-CiTPrOIC | 105,000 | 190 | 230 | | | |
| Ph-NH-CO-NH-CiTEtOIC | 21,000 | 25,000 | 22,400 | 4,740 | 104,000 | 50,000 |
| PhCH$_2$NHCONH-CiTEtOIC | | 16,800 | 11,680 | 2,340 | 105,000 | 45,000 |
| PhCH$_2$CONH-CiTEtOIC | | 15,800 | 6,730 | 3,630 | | 59,000 |
| D-Phe-NH-CiTEtOIC | | 4,240 | 3,070 | 3,070 | | 82,000 |
| Boc-D-Phe-NH-CiTEtOIC | | 1,040 | 1,090 | | | |
| L-Phe-NH-CiTEtOIC | | 1,280 | 1,340 | 3,770 | | 107,000 |
| Boc-L-Phe-NH-CiTEtOIC | | 1,090 | 1,140 | 1,620 | | |
| Ala-Ala-NH-CiTEtOIC | | 1,070 | 880 | 1,490 | | |
| Boc-Ala-Ala-NH-CiTEtOIC | | 1,530 | 970 | | | |
| (CH$_3$)$_2$CHNHCONH-CiTEtOIC | | 4,100 | 5,000 | | | |
| Naphthyl-NHCONH-CiTEtOIC | | 17,500 | 5,800 | | | |
| S-C$_6$H$_5$(CH$_3$)CHNHCONH-CiTEtOIC | | 41,300 | 21,000 | | | |
| R-C$_6$H$_5$(CH$_3$)CHNHCONH-CiTEtOIC | | 29,500 | 12,000 | | | |
| PhNHCSNH-CiTEtOIC | | | 21,400 | | | |

TABLE 1-continued

Inhibition Rates of Bovine Trypsin and Coagulation Enzymes by 7-Substituted-4-chloro-3-isothiureidoalkoxyisocoumarins[a].

| Compounds | $k_{obs}/[I]$ $(M^{-1}s^{-1})$ | | | | | |
|---|---|---|---|---|---|---|
| | Bovine Trypsin[b] | Bovine Thrombin[c] | Human Thrombin[d] | Human Factor Xa[e] | Human Factor XIa[f] | Human Factor XIIa[g] |
| m-Carboxy-PhNHCSNH-CiTEtOIC | | | 17,500 | | | |

[a]Inhibition rates were measured in 0.1M Hepes, 0.01M CaCl$_2$, pH 7.5 buffer, 8% Me$_2$SO and at 25° C.
[b]Inhibitor concentration were 1.1–4.6 μM.
[c]Inhibitor concentration were 1.2–54 μM.
[d]Inhibitor concentration were 1.2–54 μM.
[e]Inhibitor concentration were 3.6–44 μM.
[f]Inhibitor concentration were 0.7–0.8 μM.
[g]Inhibitor concentration were 3.6–4.9 μM.
[h]Data was obtained from Kam, Fujikawa, and Powers, Biochemistry 27, pp. 2547–2557 (1988).

TABLE II

Inhibition of Several Tryptases by 7-Substituted-4-chloro-3-isothiureidoalkoxyisocoumarins[a].

| Compounds | $k_{obs}/[I]$ $(M^{-1}s^{-1})$ | | | | |
|---|---|---|---|---|---|
| | Human Skin Tryptase[b] | Rat Skin Tryptase[c] | Human Lung Tryptase[d] | Human Plasmin[e] | Human r-t-PA[f] |
| NH$_2$-CiTPrOIC | | 39,000 | | | 13,000 |
| PhCH$_2$NHCONH-CiTPrOIC | 68%[g] | 270,000 | 190,000 | 5,120 | 18,000 |
| PhNHCONH-CiTPrOIC | 38,000 | 250,000 | 140,000 | | 19,000 |
| CH$_3$CONH-CiTPrOIC | | 99,000 | 60%[g] | | 7,000 |
| PhCH$_2$CH$_2$CONH-CiTPrOIC | | 170,000 | 180,000 | | 15,000 |
| PhCH$_2$CONH-CiTPrOIC | | 145,000 | 140,000 | | 9,000 |
| L-Phe-NH-CiTPrOIC | | 96,000 | 54%[g] | | 11,000 |
| Boc-L-Phe-NH-CiTPrOIC | | 150,000 | 170,000 | | 6,000 |
| PhNHCONH-CiTEtOIC | | 170,000 | 170,000 | 32,000 | 16,000 |
| PhCH$_2$NHCONH-CiTEtOIC | | 200,000 | 280,000 | | 19,000 |
| PhCH$_2$CONH-CiTEtOIC | | 120,000 | 110,000 | | 64%[g] |
| D-Phe-NH-CiTEtOIC | 62,000 | 360,000 | 60,000 | | 15,000 |
| Boc-D-Phe-NH-CiTEtOIC | | 135,000 | | | 65%[g] |
| L-Phe-NH-CiTEtOIC | | 650,000 | 260,000 | | 13,000 |
| S-C$_6$H$_5$(CH$_3$)CHNHCONH-CiTEtOIC | | | | 27,800 | |

[a]Inhibition rates were measured in 0.1M Hepes, 0.01M CaCl$_2$, pH 7.5 buffer for human plasmin; 25 mM Phosphate, 0.5M NaCl, 1 mM EDTA, pH 7.5 buffer for rat skin tryptase and 0.1M Hepes, 0.5M NaCl, pH 7.5 for human lung tryptase, human skin tryptase and r-t-PA. All enzymes were assayed with Z-Arg-SBzl (0.07 mM) in the presence of 4,4'-dithiodipyridine (0.33 mM). Reaction mixtures contained 8% Me$_2$SO and assays were performed at 25° C.
[b]Inhibitor concentrations were 0.34–0.39 μM.
[c]Inhibitor concentrations were 0.42–0.51 μM.
[d]Inhibitor concentrations were 0.42–0.47 μM.
[e]Inhibitor concentrations were 8.3–41 μM.
[f]Inhibitor concentrations were 3.5–5.0 μM, r-t-PA = recombinant-tissue plasminogen activator.
[g]Inhibition was not time dependent and the percentage was measured at 0.34–5.0 μM.

TABLE III

Inhibition of Serine Proteases by 7-Substituted-4-chloro-3-isothiureidoalkoxyisocoumarins[a].

| Compounds | $k_{obs}/[I]$ $(M^{-1}s^{-1})$ | | | |
|---|---|---|---|---|
| | PPE[b] | HLE[c] | Chymotrypsin[d] | Cathepsin G[b] |
| PhCH$_2$NHCONH-CiTPrOIC | 9%[e] | 250 | 13,430 | 50 |
| CH$_3$CONH-CiTPrOIC | NI[f] | 200 | 5,200 | 31 |
| PhCH$_2$CONH-CiTPrOIC | NI | 130 | 260,000[g] | 64 |
| PhNHCONH-CiTEtOIC | 840 | 46,000[h] 5,730 | 16,000 | 100 |
| Boc-D-Phe-NH-CiTEtOIC | 12%[f] | 3,100 | 220 | 35 |
| L-Phe-NH-CiTEtOIC | NI | NI | 8,400 | 53 |
| S-C$_6$H$_5$(CH$_3$)CHNHCONH-CiTEtOIC | 21%[f] | 5,100[h] 360 | 260 | 35 |
| R-C$_6$H$_5$(CH$_3$)CHNHCONH-CiTEtOIC | 9%[f] | 40%[i] | 360 | 145 |

[a]Inhibition rates were measured in 0.1M Hepes, 0.05M NaCl, pH 7.5 buffer, 8–9% Me$_2$SO and at 25° C. Substrates were Suc-Ala-Ala-Ala-Na (0.48 mM) for PPE; MeO-Suc-Ala-Ala-Pro-Val-NA (0.24 mM) for HLE; Suc-Val-Pro-Phe-NA (0.48 mM) for chymotrypsin and cathepsin G.
[b]Inhibitor concentrations were 33–46 μM.
[c]Inhibitor concentrations were 2.1–42 μM.
[d]Inhibitor concentrations were 0.9–43 μM.
[e]Percentage of inhibition was obtained after 20 min incubation of enzyme with inhibitor.
[f]No inhibition.
[g]Second order of rate constant was obtained at equal molar concentrations of enzyme and inhibitor.
[h]Inhibition was biphasic.
[i]Percentage of inhibition was obtained after 5 min incubation of enzyme with inhibitor.

TABLE IV

Effect of 7-Substituted-4-chloro-3-(2-isothiureidoethoxy) isocoumarins on PT and APTT in Pig Plasma[a].

| Compounds | [I] (μM) | PT (sec) | APTT (sec) |
| --- | --- | --- | --- |
| Control | 0 | 18.6 | 17.7 |
| PhNHCONH-CiTEtOIC | 16 | 28.5 | >120 |
|  | 32 | 58.3 |  |
| PhCH$_2$NHCONH-CiTEtOIC | 32 | 31.1 | >120 |
| S-C$_6$H$_5$(CH$_3$)CHNHCONH-CiTEtOIC | 32 | 30.0 | >120 |
| R-C$_6$H$_5$(CH$_3$)CHNHCONH-CiTEtOIC | 32 | 26.2 | >120 |

[a]Average of two trials

TABLE V

Hydrolysis Rates of 7-Substituted-4-chloro-3-isothiureidoalkoxyisocoumarins[a].

| Compounds | t$_{\frac{1}{2}}$ (min) |
| --- | --- |
| NH$_2$-CiTPrOIC | 90 |
| PhCH$_2$NHCONH-CiTPrOIC | 148 |
| PhNHCONH-CiTPrOIC | 148 |
| CH$_3$CONH-CiTPrOIC | 68 |
| PhCH$_2$CH$_2$CONH-CiTPrOIC | 66 |
| PhCH$_2$CONH-CiTPrOIC | 61 |
| PhNHCONH-CiTEtOIC | 108 |

[a]Half-life for the hydrolysis was measured in 0.1M Hepes, 0.01M CaCl$_2$, pH 7.5 buffer, 8% Me$_2$SO and at 25° C.

What is claimed is:

1. A compound of the formula:

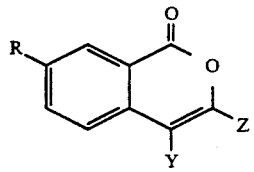

or a pharmaceutically acceptable salt thereof, wherein

Z is selected form the group consisting of C$_{1-6}$ alkoxy with an amino group attached to the alkoxy group, C$_{1-6}$ alkoxy with an isothiureido group attached to the alkoxy group, C$_{1-6}$ alkoxy with a guanidino group attached to the alkoxy group, C$_{1-6}$ alkoxy with an amidino group attached to the alkoxy group, C$_{1-6}$ alkyl with an amino group attached to the alkyl group, C$_{1-6}$ alkyl with an isothiureido group attached to the alkyl group, C$_{1-6}$ alkyl with an guanidino group attached to the alkyl group, C$_{1-6}$ alkyl with an amidino group attached to the alkyl group, R is selected for the group consisting of O=C=N—, S=C=N—, AA—NH—, AA—AA—NH—, AA—O—, AA—AA—O—, M—NH—, M—AA—NH—, M—AA—AA—NH—, M—O—, M—AA—O—, or M—AA—AA—O—, wherein AA represents alanine, valine, leucine, isoleucine, methionine, phenylalanine, glucine, serine, threonine, cysteine, tyrosine, asparagine, glutamine, aspartic acid, glutamic acid, lysine, arginine, beta-alanine, norleucine, norvaline, alpha-aminobutyric acid, epsilon-aminocaproci acid, citrulline, hydroxyproline, ornithine or sarcosine, wherein M represents NH$_2$—CO—, NH$_2$—CS—, NH$_2$—SO$_2$—, X—NH—CO—, X—NH—CS—, X—NH—SO$_2$—, X—CO—, X—CS—, X—SO$_2$—, X—O—CO—, X—O—CS—, wherein X represents C$_{1-6}$ alkyl, C$_{1-6}$ fluoroalkyl, C$_{1-6}$ alkyl substituted with K, or C$_{1-6}$ fluoroalkyl substituted with K, wherein K represents halogen, COOH, OH, CN, NO$_2$, NH$_2$, C$_{1-6}$ alkoxy, C$_{1-6}$alkylamine, C$_{1-6}$ dialkylamine, or C$_{1-6}$ alkyl—O—CO—, Y is selected from the group consisting of H, halogen, trifluoromethyl, methyl, OH and methoxy.

2. The compound of claim 1 wherein X represents phenyl, phenyl substituted with J, phenyl disubstituted with J, phenyl trisubstituted with J, naphthyl, naphthyl substituted with J, naphthyl disubstituted with J, or naphthyl trisubstituted with J, wherein J represents halogen, COOH, OH, CN, NO$_2$, NH$_2$, C$_{1-6}$ alkoxy, C$_{1-6}$ alkyl, C$_{1-6}$ alkylamine, C$_{1-6}$ dialkylamine, or C$_{1-6}$ alkyl—O—CO—.

3. The compound of claim 1 wherein X represents C$_{1-6}$ alkyl with an attached phenyl group, or C$_{1-6}$ alkyl with two attached phenyl groups.

4. The compound of claim 1 wherein X represents C$_{1-6}$ alkyl with an attached phenyl group substituted with J, or C$_{1-6}$ alkyl with two attached phenyl groups substituted with J.

* * * * *